United States Patent [19]

McFall et al.

[11] Patent Number: 5,730,738
[45] Date of Patent: Mar. 24, 1998

[54] ABSORBENT ARTICLE WITH ANGLED BAND STRUCTURAL ELASTIC-LIKE FILM CUFFS

[75] Inventors: Ronald Ray McFall, Westchester; John Joseph Curro, Cincinnati; Allison Kay Hunter, Westchester, all of Ohio; Jason Matthew Orndorff, Lawrenceburg, Ind.; Kenji Ohshima, Osaka; Hiroaki Shikata, Kobe, both of Japan

[73] Assignee: The Procter & Gamble Company, Cincinnati, Ohio

[21] Appl. No.: 567,499

[22] Filed: Dec. 4, 1995

[51] Int. Cl.$^6$ .................................................. A61F 13/15
[52] U.S. Cl. ................... 604/387; 604/385.1; 604/385.2
[58] Field of Search ........................ 604/358, 385.1, 604/385.2, 386, 387

[56] References Cited

U.S. PATENT DOCUMENTS

| | | |
|---|---|---|
| Re. 34,920 | 4/1995 | Aziz et al. |
| 3,575,174 | 4/1971 | Mogor. |
| 4,579,556 | 4/1986 | McFarland. |
| 4,678,527 | 7/1987 | Ulman .................... 156/213 |
| 4,701,177 | 10/1987 | Ellis et al. |
| 4,758,241 | 7/1988 | Papajohn .................. 604/387 |
| 4,770,657 | 9/1988 | Ellis et al. |
| 4,834,739 | 5/1989 | Linker, III et al. ......... 604/385.1 |
| 4,854,984 | 8/1989 | Ball et al. ................. 156/73.5 |
| 4,944,735 | 7/1990 | Mokry .................... 604/385.2 |
| 5,032,121 | 7/1991 | Mokry .................... 604/385.2 |
| 5,074,856 | 12/1991 | Coe et al. ................. 604/385.1 |
| 5,234,422 | 8/1993 | Sneller et al. ............. 604/385.2 |
| 5,308,346 | 5/1994 | Sneller et al. ............. 604/385.2 |
| 5,312,386 | 5/1994 | Correa et al. .............. 604/379 |
| 5,346,486 | 9/1994 | Osborn, III et al. ........ 604/385.1 |
| 5,387,210 | 2/1995 | Murakami ................. 604/396 |
| 5,413,569 | 5/1995 | Yamamoto ................ 604/385.2 |
| 5,445,627 | 8/1995 | Mizutani et al. ........... 604/387 |
| 5,490,847 | 2/1996 | Correa et al. .............. 604/387 |
| 5,518,801 | 5/1996 | Chappell et al. ........... 604/358 |
| 5,569,234 | 10/1996 | Buell et al. ............... 604/385.1 |
| 5,571,096 | 11/1996 | Dobrin et al. ............. 604/385.1 |

FOREIGN PATENT DOCUMENTS

| | | | |
|---|---|---|---|
| 5137750 | 6/1993 | Japan | 604/387 |
| 5220191 | 8/1993 | Japan | 604/387 |
| H 5-86323 | 11/1993 | Japan. | |
| WO 95/03765 | 2/1995 | WIPO. | |
| WO 95/08972 | 4/1995 | WIPO. | |
| WO/96/23471 | 8/1996 | WIPO. | |

*Primary Examiner*—John G. Weiss
*Assistant Examiner*—K. M. Reichle
*Attorney, Agent, or Firm*—Edward J. Milbrada; Jeffrey V. Bamber; Steven W. Miller

[57] ABSTRACT

Disclosed is an absorbent article, such as a sanitary napkin, incontinent device, or the like. The absorbent article includes a liquid pervious topsheet, a liquid impervious backsheet, and an absorbent core that lies between the topsheet and the backsheet. The absorbent article further includes a pair of longitudinally extending bands of web material positioned on the body surface of the topsheet on each side of a longitudinal centerline of the absorbent article and joined to at least one of the topsheet and the backsheet in a longitudinally elastically elongated state. The bands of web material include first and second regions which are visibly distinct from each other. The first region has at least two substantially planar portions and the second has a plurality of rib elements. In a particularly preferred embodiment of the invention, at least one of the substantially planar portions of the first region of the bands of web material extends in a substantially longitudinal direction and at least one other of the substantially planar portions of the first region of the bands of web material is oriented at an angle with respect to the longitudinal direction. Alternative embodiments of the present invention can also have flaps which extend laterally outward from a side edge of the central absorbent body positioned at least in a middle region of the absorbent article.

5 Claims, 12 Drawing Sheets

ABSORBENT ARTICLE WITH ANGLED BAND STRUCTURAL ELASTIC-LIKE FILM CUFFS

FIELD OF THE INVENTION

This invention relates to disposable absorbent articles such as sanitary napkins, incontinent devices, and the like. More particularly, this invention is directed to a sanitary napkin having cuffs for preventing lateral flow of bodily fluids, such as menses.

BACKGROUND OF THE INVENTION

As is well known, a disposable absorbent article, such as a sanitary napkin, has a liquid pervious topsheet, a liquid impervious backsheet, and an absorbent core disposed between the topsheet and the backsheet. Such an absorbent article should conform to the wearer's urogenital region, and be able to prevent leakage of body fluids, particularly in the lateral direction. One means of reducing leakage and conforming to a wearer's urogenital region is to provide for the absorbent article to be cup-shaped during use. Such absorbent articles can be further provided with cuffs to provide a barrier for reduction of lateral leakage of bodily fluids.

Such approaches are known to the art. For example, one means for making the absorbent article cup-shaped and forming cuffs, as stated above, is to shape the topsheet, the core and the backsheet themselves such that the absorbent article takes the cup-like form, and the topsheet and/or the backsheet forms the cuffs on both sides of the longitudinally central portion of the absorbent article. Such formed absorbent articles are described in U.S. Pat. Nos. 3,575,174, 4,678,527, and 4,834,739. Absorbent articles of this type have problems such as: 1) increased manufacturing cost because the topsheet, the core and the backsheet have to be shaped to a required form and (2) the free end of the cuff contacts the wearer's skin and may cause wearer discomfort when such an absorbent article is worn because the portion comprising the cuff has no stretch properties.

A second approach to making an absorbent article cup-shaped and forming the cuffs is to join band-like elastic pieces, in an elastically elongated state, to the topsheet and/or the backsheet adjacent both longitudinal edges of the absorbent article. The use of a rubber strip or a thermoplastic elastomeric strip as the band-like elastic piece has been proposed. Such absorbent articles are described in U.S. Pat. Nos. 4,579,556, 4,701,177, 4,758,241, 4,770,657, 4,944,735, 5,032,121, 5,074,856, and 5,312,386. In an absorbent article equipped with such band-like elastic pieces, the topsheet, core, and backsheet are shaped like a cup, and the topsheet and/or the backsheet forms the cuffs, due to the contracting action of the band-like elastic pieces. While the stretch properties of absorbent articles of this second type result in improved comfort during wear when compared to absorbent articles of the first type, such absorbent articles are expensive to produce because: (1) the use of a band-like elastic piece made from a relatively expensive rubber or thermoplastic elastomeric is required, (2) additional material is required to accommodate the band-like elastic pieces. Further, such cuffs tend to become flattened (with a resulting increase in risk of leakage) as the absorbent article is pulled to a more flat-out configuration such as may happen with increasing wearer body dimensions.

A third approach for making the absorbent article cup-shaped and forming the cuffs is to thermally bond the longitudinally opposite ends and the laterally outward portion of a thermoplastic elastic piece, in an elastically elongated state, to appropriate sites on the upper surface of the topsheet. The topsheet is also joined, as required, to the core and the backsheet. In an absorbent article equipped with such elastic pieces, the topsheet, core and backsheet are shaped like the cup due to the contracting action of the elastic pieces. On both sides of the longitudinal central portion, the elastic pieces are caused to extend upwardly inclinedly in a widthwise inward direction, forming the cuffs. Such a third proposal is disclosed in Japanese Laid-Open Utility Model Publication No. 86323/93. In this type of absorbent article, the thermoplastic elastic pieces themselves, which are thermally bonded to the topsheet, form cuffs on both sides of the longitudinal centerline. Moreover, thermal bonding can be carded out relatively simply. Thus, manufacturing cost will be lower than either of the first two types of absorbent articles. However, such absorbent articles may be uncomfortable when they are worn because the elastic material is a film which can occlude a relatively large portion of a wearer's skin. Further, thermoplastic, elastic materials are relatively expensive when compared to other components of the absorbent article and, because they are a different material than the topsheet, they are sometimes difficult to thermally bond to the other components of the absorbent article. Both of these aspects tend to increase manufacturing cost.

Thus, it is an object of the present invention to provide an absorbent article which takes the form of a cup as a whole, forms upwardly extending cuffs on both sides of the longitudinal centerline thereof wherein such cuffs remain upstanding even when the absorbent article is pulled into a substantially flat-out configuration, and yet is comfortable when worn. It is a further object of the present invention to provide such an absorbent article that can be manufactured for a satisfactorily low cost when compared to absorbent articles having neither cup-like form or cuffs. A related object of the present invention is to provide a simple and inexpensive manufacturing process for such an absorbent article.

SUMMARY OF THE INVENTION

Disclosed herein is an absorbent article, such as a sanitary napkin, incontinent device, or the like. The absorbent article comprises a liquid pervious topsheet, a liquid impervious backsheet joined to the topsheet, and an absorbent core disposed between the topsheet and the backsheet. The absorbent article has a middle region and a pair of end regions. The absorbent article further comprises a pair of longitudinally extending bands of web material disposed on the body surface of the topsheet on each side of the longitudinal centerline of the absorbent article. The bands of web material are joined to at least one of the topsheet and the backsheet in a longitudinally elastically elongated state. The bands of web material comprise first and second regions which are visibly distinct from each other. The first region comprises at least two substantially planar portions and the second region comprises a plurality of rib elements. The bands of web material provide a contractive force which causes the topsheet, the core and the backsheet in each of the end regions to extend upwardly, inclinedly away from the plane of the middle region. The contractive force further causes the bands of web material to extend upwardly away from the topsheet forming cuffs on both sides of the middle region of the absorbent article. In a particularly preferred embodiment of the present invention, at least one of the substantially planar portions of the first region of the bands of web material extends in a substantially longitudinal direction and at least one other of the substantially planar portions of the first region of the bands of web material is oriented at an angle with respect to the longitudinal direction, especially when the bands of material are placed in a flattened and extended condition. Alternative embodiments of the present invention can be further provided with laterally extending flaps positioned at least in the middle region of the absorbent article and extending laterally outward from a side edge of the central absorbent body.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which reference numerals identify like elements and wherein:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united or joined together to form a coordinated entity so that they do not require separate manipulative parts like a separate holder and pad. As used herein, the term "joined" encompasses configurations whereby an element is directly secured to another element by affixing the element directly to the other element, and configurations whereby the element is indirectly secured to the other element by affixing the element to an intermediate member(s) which in turn is affixed to the other element.

Figure 1:
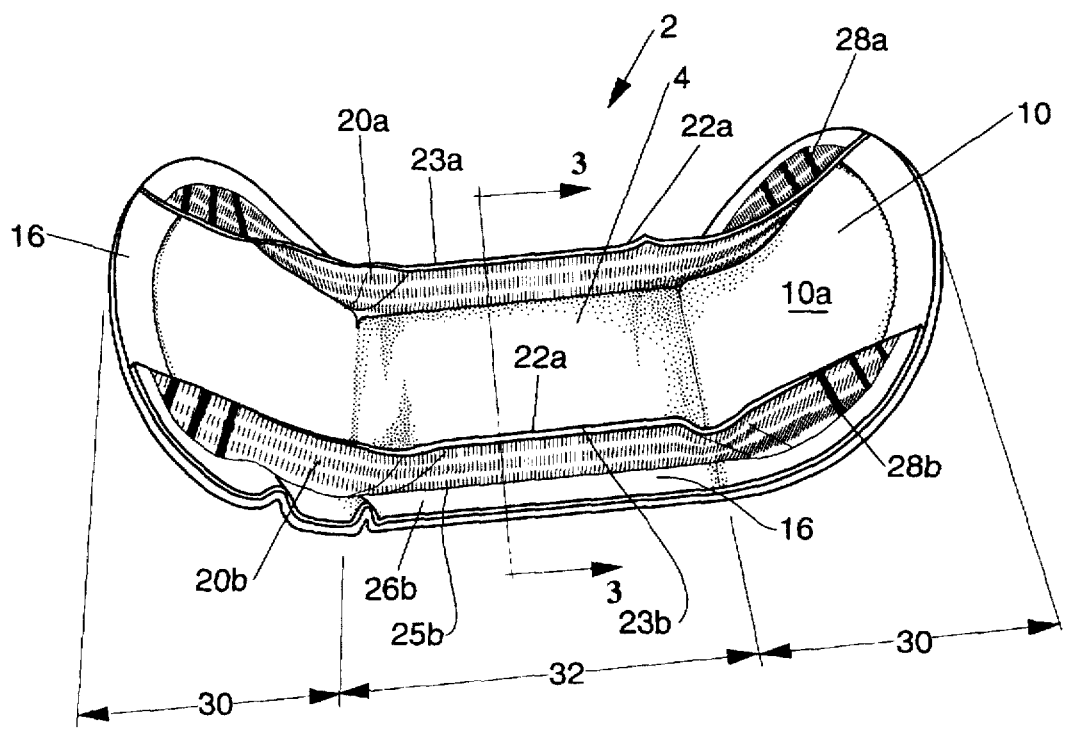
FIG. 1 is a perspective view showing a basic embodiment of a sanitary napkin according to the present invention.

A preferred embodiment of a unitary disposable absorbent article of the present invention is the sanitary napkin 2, shown in FIG. 1. As used herein, the term "sanitary napkin" refers to an absorbent article which is worn by females adjacent to the pudendal region, generally external to the urogenital region, and which is intended to absorb and contain menstrual fluids and other discharges from the wearer's body (e.g., blood, menses, and urine). Interlabial devices which reside partially wig and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as diapers, incontinence pads, and the like.

Figure 2:
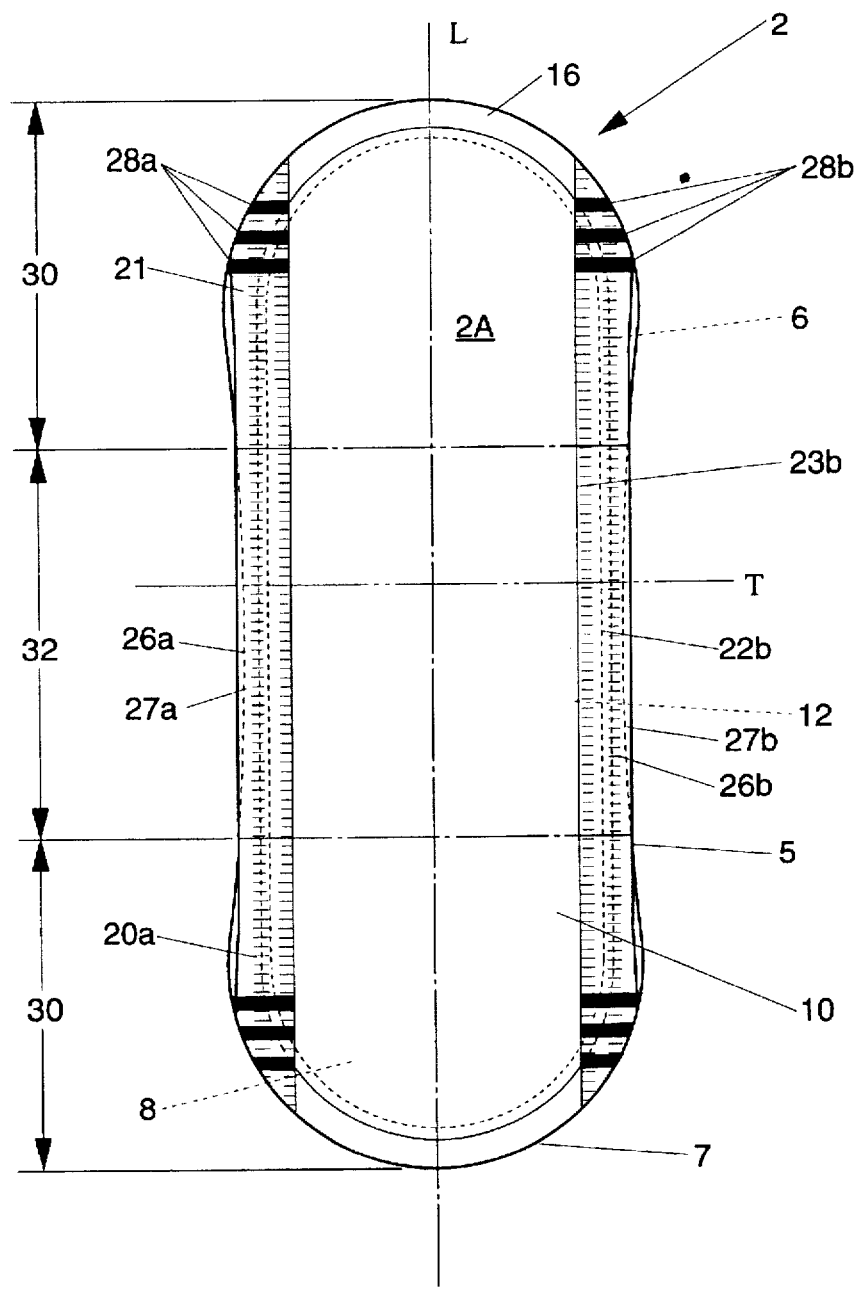
FIG. 2 is a plan view showing the sanitary napkin of FIG. 1 in its flat-out state with the cuffs elongated.
Figure 3:
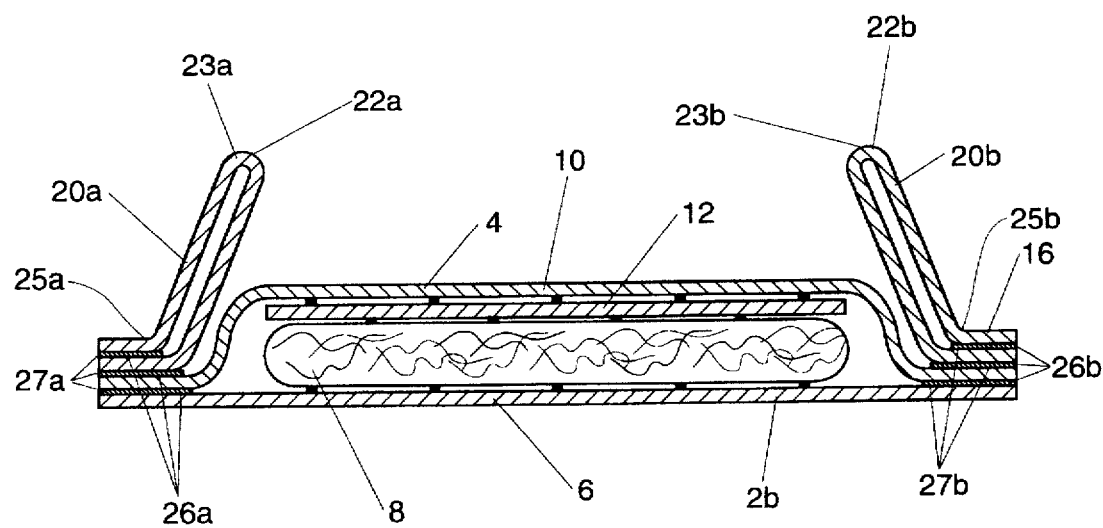
FIG. 3 is a cross sectional view taken on line 3—3 of FIG. 1.

FIGS. 1 to 3 show a sanitary napkin 2, a preferred embodiment of an absorbent article constructed in accordance with the present invention. The sanitary napkin 2, as will be understood from the following description, is not in a substantially flat form, but is cup-shaped as illustrated in FIG. 1, due to the contracting action of a SELF web as will be described below. In FIG. 2, the entire sanitary napkin 2 is shown in a substantially flat state with its cuffs elongated. The sanitary napkin 2 shown in FIGS. 1 to 3 has a liquid pervious topsheet 4, a liquid impervious backsheet 6, and an absorbent core 8 positioned between the topsheet 4 and the backsheet 6. The sanitary napkin 2 further comprises longitudinally extending cuffs 20, the cuffs 20 comprising a SELF web. As will be described below, the elastic-like properties of a SELF web cause the distal edge 23 of the cuffs 20 to extend upward above the plane of the topsheet 4 and provide the sanitary napkin 2 of the present invention with a cup-like configuration The sanitary napkin 2 has two surfaces, a body-contacting surface or "body surface" 2A and a garment surface 2B. In a similar manner, the body surface of other components of the sanitary napkin 2 having a body surface will be referred to using the reference number for the component followed by the letter A and any reference to the garment surface of a component will use the reference number for the component followed by the letter B. The sanitary napkin 2 is shown in FIG. 2 as viewed from its body surface. The body surface 2A is intended to be worn adjacent to the body of: the wearer. At least a potion of the body surface 2A comprises the topsheet 4. The garment surface 2B is on the opposite side of the sanitary napkin 2 and is intended to be placed adjacent to the wearer's undergarments when the sanitary napkin 2 is worn. At least a portion of the garment surface 2B comprises the backsheet 6. The sanitary napkin 2 has two centerlines, a longitudinal centerline L and a transverse centerline T. The term "longitudinal", as used herein, refers to a line, axis or direction in the plane of the sanitary napkin 2 that is generally aligned with (e.g., approximately parallel to) a vertical plane which bisects a standing wearer into left and right body halves when the sanitary napkin 2 is worn. The terms "transverse" or "lateral" as used herein, are interchangeable, and refer to a line, axis or direction which lies within the plane of the sanitary napkin 2 that is generally perpendicular to the longitudinal direction. FIG. 2 also shows that the sanitary napkin 2 has a periphery 21 which is defined by the outer edges of the sanitary napkin 20 in which the longitudinal edges are designated 5 and the end edges are designated 7. As can also be seen in FIGS. 1 and 2, the sanitary napkin 2 comprises longitudinally opposite end regions 30 and a central region 32.

The topsheet 4 should permit bodily discharges from the wearer to rapidly penetrate its thickness for absorption by the absorbent core 8, and should not cause excessive discomfort to the wearer when it is in contact with the wearer's skin. The topsheet 4 forms at least a portion of the body surface 2A of the sanitary napkin 2.

The topsheet 4 can be formed from materials, such as woven or nonwoven fabrics comprising natural or synthetic fibers; apertured thermoplastic films; porous foams; reticulated foams; reticulated thermoplastic films; and thermoplastic scrims. In the preferred embodiment shown in FIGS. 1 to 3, the topsheet 4 comprises a composite topsheet comprising a primary topsheet layer 10 and a secondary topsheet layer 12 (seen most clearly in FIG. 3). The primary topsheet layer 10 and the secondary topsheet layer 12 are joined to form composite topsheet 4 using means familiar to those skilled in the art such as adhesive bonding, ultrasonic welding, or thermal bonding which is carried out in a multiplicity of discrete areas. An exemplary means for joining the primary topsheet layer 10 to the secondary topsheet layer 12 to form composite topsheet 4 comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. The disclosure of each of these patents is incorporated herein by reference. In a preferred embodiment, the secondary topsheet layer 12 may be joined to the primary topsheet layer 10 to form composite topsheet 4 by fusion bonds as is more fully described in U.S. patent application Ser. No. 07/810,774, filed Dec. 17, 1991 in the names of Cree, et al and published as PCT Application Serial No. WO 93/11725 on Jun. 24, 1993, the disclosure of which is incorporated herein by reference.

As can be seen in FIG. 2, the primary topsheet layer 10 preferably has a substantially rectangular configuration. A portion of the primary topsheet layer 10 extends convexly arcuately outward to form a portion of the end edges 7 of the sanitary napkin 2. Preferably, the portion of the longitudinal edges of the primary topsheet 10 that lies in each of the end regions 30 is substantially linear and parallel to the longitudinal centerline L.

A suitable primary topsheet layer 10 may be manufactured from a wide range of materials such as woven and nonwoven materials; polymeric materials such as apertured formed thermoplastic films, apertured plastic fills, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred primary topsheet layer 10 comprises an apertured formed film. Apertured formed fills are preferred for the primary topsheet layer 10 because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, which issued to Thompson on Dec. 30, 1975; U.S. Pat. No. 4,324,246, which issued to Mullane, et al. on Apr. 13, 1982; U.S. Pat. No. 4,342,314, which issued to Radel, et al. on Aug. 3, 1982; U.S. Pat. No. 4,463,045, which issued to Ahr et al. on Jul. 31, 1984; and U.S. Pat. No. 5,006,394, which issued to Baird on Apr. 9, 1991. The disclosure of each of these patents is incorporated herein by reference. The preferred primary topsheet layer 10 for the present invention is the formed film described in one or more of the above patents and marketed on sanitary napkins by The Procter & Gamble Company of Cincinnati, Ohio as "DRI-WEAVE".

In a preferred embodiment of the present invention, the body surface 10A of the formed film primary topsheet layer 10 is hydrophilic so as to help liquid to transfer through the composite topsheet 4 faster than if the body surface was not hydrophilic so as to diminish the likelihood that menstrual fluid will flow off the primary topsheet layer 10 rather than flowing into and being absorbed by the absorbent core. In a preferred embodiment, surfactant is incorporated into the polymeric materials of the formed film primary topsheet layer 10 such as is described in U.S. patent application Ser. No. 07/794,745, filed on Nov. 19, 1991 by Aziz, et al., and published as PCT Application Serial No. WO 93/09741 on May 27, 1993 the disclosure of which is incorporated herein by reference. Alternatively, the body surface of the primary topsheet layer 10 can be made hydrophilic by treating it with a surfactant such as is described in U.S. Pat. No. 4,950,264, issued to Osborn, III on Aug. 21, 1990, the disclosure of which is incorporated herein by reference.

The secondary topsheet layer 12 lies between the primary topsheet layer 10 and the absorbent core 8 and is joined to the inner surface of the primary topsheet layer 10 to form composite topsheet 4 as described above. The secondary topsheet layer 12 of composite topsheet 4 is similar in shape to the primary topsheet layer 10, but preferably with smaller longitudinal and transverse dimensions than the longitudinal and transverse dimensions of the primary topsheet layer 10. That is, the periphery of the primary topsheet layer 10 is larger than the periphery of the secondary topsheet layer 12 of composite topsheet 4. The secondary topsheet layer 12 of composite topsheet 4 disperses bodily fluids, which have passed through the primary topsheet layer 10, mainly in the longitudinal direction, such that the absorbent core 8 is more fully utilized.

The secondary topsheet layer 12 of composite topsheet 4 may serve several functions including improving wicking of exudates over and into the absorbent core. There are several reasons why the improved wicking of exudates is important, including providing a more even distribution of the exudates throughout the absorbent core and allowing the sanitary napkin 2 to be made relatively thin. (The wicking referred to herein may encompass the transportation of liquids in one, two or all directions (i.e., in the x-y plane and/or in the z-direction.) The secondary topsheet layer 12 of composite topsheet 4 may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of sanitary napkins having a secondary topsheet layer 12 of composite topsheet 4 are more fully described in the above-referenced U.S. Pat. No. 4,950,264 and the above-referenced Cree application. The disclosure of each of these publications is incorporated herein by reference. Preferably, the secondary topsheet layer 12 of composite topsheet 4 is formed from a natural or synthetic nonwoven fabric. A particularly preferred nonwoven material for the secondary topsheet layer 10 comprises an air laid tissue having a basis weight of about 35 grams per square meter (gsm). A suitable material is available from Merfin Hygiene Products Ltd., Delta, BC, Canada. Alternative nonwoven materials suitable for forming the secondary topsheet layer 12 of composite topsheet 4 include a nonwoven fabric of spunbonded polypropylene fibers available from the Fiberweb Corporation of Simpsonville, S.C. under the tradename CELESTRA and a nonwoven fabric formed of bicomponent fibers which have a polyethylene sheath and a polyurethane core, which is available from the Havix Company, of Japan, as S2416.

The backsheet 6 is intended to prevent bodily fluids absorbed by the absorbent core 8 from flowing out of the sanitary napkin and soiling the wearer and/or the wearer's clothing. Preferably, the backsheet 6 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 6 prevents the exudates absorbed and contained in the absorbent core 8 from wetting articles which contact the sanitary napkin 2 such as pants, pajamas and undergarments. The backsheet 6 may, thus, comprise a woven or nonwoven material, polymeric films such as thermoplastic films of polyethylene or polypropylene, or composite materials such as a film-coated nonwoven material. Preferably, backsheet 6 can comprise a flexible liquid impervious thermoplastic film such as a polyolefinic film. Particularly preferred films for forming the backsheet 6 include a low density polyethylene film having a caliper of from about 0.01 mm (0.4 mils) to about 0.05 mm (2.0 mils), preferably about 0.025 mm (1.0 mil). Such a polyethylene film is sold by the Ethyl Corp., Visqueen Division, of Terre Haute, Ind., as Model XP-39385 and by the Clopay Corp. of Cincinnati, Ohio as SOFLEXX 1401.

As shown most clearly in FIG. 2, the backsheet 6 has a shape and dimensions which are substantially the same as those of the primary topsheet layer 10 of composite topsheet 4. The primary topsheet layer 10 of composite topsheet 4 and the backsheet 6 are bonded uninterruptedly throughout their periphery (i.e., throughout the periphery 21 of sanitary napkin 2). This area of peripheral bonding 16 is shown most clearly in FIG. 2. Preferably, the primary topsheet layer 10 and the backsheet 6 are joined in the area of peripheral bonding 16 by at least one seal formed by the application of pressure, with or without heat, commonly referred to as a crimp seal. Alternatively, the primary topsheet layer 10 and the backsheet 6 may be joined together in any other suitable manner, such as bonding with an adhesive.

In use, the sanitary napkin 2 can be held in place by any support means or attachment means (not shown) well-known for such purposes. Preferably, the sanitary napkin is placed in the user's undergarment or panty and secured thereto by a fastener such as an adhesive. The adhesive provides a means for securing the sanitary napkin in the crotch portion of the panty. Thus, a portion or all of the garment surface of the backsheet 6 may be coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio and Instant Lock 34-2823 manufactured by the National Starch and Chemical Company of Bridgewater, N.J. Suitable adhesive fasteners are also described in U.S. Pat. No. 4,917,697 issued to Osborn III, et al. on Apr. 17, 1990, the disclosure of which is incorporated herein by reference. Before the sanitary napkin is placed in use, the pressure-sensitive adhesive is typically covered with a removable release liner in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. Preferably, a release liner is used which also serves as an individual package for the sanitary napkin 2. Suitable release liners that also serve as a package for an individual sanitary napkin are described in U.S. Pat. No. 4,556,146, issued to Swanson, et al., the disclosure of which is incorporated herein by reference. The sanitary napkin of the present invention is used by removing the release liner and thereafter placing the sanitary napkin in a panty so that the adhesive contacts the panty. The adhesive maintains the sanitary napkin in its position within the panty during use.

The absorbent core 8, which is disposed between the topsheet 4 and the backsheet 6, absorbs and retains bodily fluids that have penetrated the topsheet 4 after discharge by a wearer. The absorbent core 8 may be any absorbent means which is capable of absorbing or retaining liquids (e.g., menses and/or urine). The absorbent core 8 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinence pads, pantiliners, regular sanitary napkins, or overnight sanitary napkins. Exemplary absorbent structures suitable for use as the absorbent core of the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; European Patent Application No. 0 198 683, The Procter & Gamble Company, published Oct. 22, 1986 in the name of Duenk, et al.; and U.S. Pat. No. 5,009,653 issued to Osborn, III, on Apr. 23, 1991. The disclosure of each of these patents is incorporated herein by reference.

The longitudinal and transverse dimensions of core 8, as it is shown in FIG. 2, are preferably smaller than the longitudinal and transverse dimensions of the primary topsheet layer 10 and the backsheet 6. Preferably, core 8 lies within the region defined by the areas of peripheral bonding 16 between the primary topsheet layer 10 and the backsheet 6. More preferably, the secondary topsheet layer 12 of composite topsheet 4 is disposed between the core 8 and the primary topsheet layer 10 and the longitudinal and transverse dimensions of the secondary topsheet layer 12 of composite topsheet 4 are somewhat larger than or substantially equal to the longitudinal and transverse dimensions of core 8.

The top surface (i.e., the surface closest to the topsheet 4) of the core 8 is joined to the lower surface of the secondary topsheet layer 12 of composite topsheet 4, while the lower surface of the core 8 is joined to the inner surface or top surface of the backsheet 6. The core 8 may be joined to the secondary topsheet layer 12 of composite topsheet 4 and to the backsheet 6 using means known to those skilled in the art (not shown) such as by bonding using a suitable adhesive. Preferably the core 8 is joined to the secondary topsheet 12 and to the backsheet 6 using an open pattern network of filaments comprises several lines of adhesive filaments swirled into a spiral pattern as discussed above. Adhesives which have been found to be satisfactory are manufactured by H. B. Fuller Company of St. Paul, Minn. under the designation HL-1258 or H-2031. Alternatively, the core 8 may be joined to the secondary topsheet layer 12 of composite topsheet 4 and/or the backsheet 6 in any other suitable manner, such as by ultrasonic welding or thermal bonding.

With further reference to FIGS. 1 to 3, the preferred embodiment of the sanitary napkin 2 of the present invention further comprises a pair of cuffs 20a and 20b. In a similar manner, pairs of elements that are disposed on opposite sides of the sanitary napkin 2 will be referred to using the reference number for the element followed either by the lower case letter a or the letter b. Each of the cuffs 20a and 20b is disposed on the body surface of the topsheet 4 in an elongated state, and is joined to the topsheet 4 in that elongated state as is described below. As will be easily understood by reference to FIG. 3, the web comprising each of the cuffs 20a and 20b is first folded back along longitudinally extending lines 22a and 22b to provide a two-layer configuration and to form distal edges 23a and 23b and opposed proximal edges 25a and 25b. The folded cuffs 20 are elongated to a predetermined length and disposed on topsheet 4, one cuff 20 on each side of centerline L, with the distal edges 23a and 23b directed inwardly toward and substantially parallel with longitudinal centerline L and the proximal edges 25a and 25b lying juxtaposed with the longitudinal edges 5 of topsheet 4.

Each of the cuffs 20a and 20b has the respective layers of the two-layer structure thereof joined together adjacent the proximal edges 25a and 25b thereof, and is further bonded, using first bonding means 26a and 26b, to the primary topsheet layer 10 of the topsheet 4, throughout that portion of each cuff 20a and 20b that lies within the area of peripheral bonding 16 lying along the longitudinal edges 5. Preferably, such first bonding means 26 comprises the application of pressure, with or without heat, commonly referred to as a crimping, although other means, such as, adhesive bonding or ultrasonic bonding are also suitable. A portion of each cuff 20a and 20b is then bonded to the underlying portion of the cuff 20 with second bonding means 27a and 27b. Second bonding means 27 also bonds the cuffs 20 to the primary topsheet layer 10 in that portion of the peripheral bonding area 16 adjacent the end edges 7. Preferably, such second bonding means 27 are same the as those used to comprise first bonding means 26. Optimally, first bonding means 26 and second bonding means 27 combine such that the area of peripheral bonding 16, which joins the topsheet 4 to the backsheet 6, is formed at the same time the cuffs 20 are bonded to the topsheet 4. Alternatively, the cuffs 20a and 20b can be C-folded as described above, disposed on the topsheet 4 in an elongated configuration, and bonded to the topsheet in a single crimping step that combines the effects of first bonding means 26 and second bonding means 27 while forming the area of peripheral bonding 16.

The portion of the cuffs 20 lying in end regions 30 are further joined to underlying structure using tertiary bonding means 28 at a plurality of spaced apart sites. Importantly, at least portion of the plurality of sites for tertiary bonds 28a and 28b overlie core 8 to prevent the corners of sanitary napkin 2 from bending in toward the longitudinal centerline L. The tertiary bonds 28a and 28b disrupt the "elastic-like" structure of the cuffs 20a and 20b (discussed below) so there is no contractive force in end regions 30 to cause the corners to bend in. Further, cuffs 20a and 20b are locally joined to the relatively stiff core 8 via the primary topsheet layer 10, effectively transmitting the contracting action of cuffs 20a and 20b to core 8. This transmission of forces further resists the undesirable local bending in the four corners of the sanitary napkin 2. Consequently, the topsheet 4, backsheet 6 and core 8 are caused to extend inclinedly upward away from the plane of the central region 32 in each of the end regions 30, forming the desired cup-like configuration. For example, three sites of tertiary bonds 28a and 28b are shown in FIGS. 1 and 2. As can be seen in FIG. 2, one of such bonds 28a and one bond 28b do not overlie core 8. While the remaining two bonds 28a and 28b do overlie core 8. Preferably tertiary bonds 28 comprise dynamic mechanical bonds as described in U.S. Pat. No. 4,854,984, issued to Ball, et al. on Aug. 8, 1989. Alternatively, other suitable methods, such as, thermal bonding, crimping, or ultrasonic welding may be employed as tertiary bonding means 28 to join the cuffs 20a and 20b to underlying structure in the end regions 30.

As noted above, cuffs 20a and 20b are disposed on the topsheet 4 in an elongated state, and are bonded thereto by bonding means 26a and 26b, 27a and 27b, and in spaced apart sites 28a and 28b. When the force that has maintained the cuffs 20a and 20b in an elongated condition is released, the unbonded portions of the cuffs 20a and 20b contract, and thus, the cuffs 20a and 20b, at least partially, return their original lengths. This contracting action generated in the cuffs 20a and 20b, causes the topsheet 4, the backsheet 6 and the core 8 to be displaced so that end regions 30 lie above central region 32 as is clearly illustrated in FIG. 1. Thus, the sanitary napkin 2 is brought into the shape of a cup as a whole. In addition, in central region 32, the distal edge 23 of each of the cuffs 20a and 20b extends upward and away from the plane of the topsheet 4 forming a barrier which impedes the lateral flow of bodily fluids with a resulting reduction in leakage along the longitudinal edges 5 of the sanitary napkin 2. The degree of elongation imparted to the cuffs 20a and 20b when they are disposed on the topsheet 4 and thermally bonded thereto depends on the overall configuration and dimensions of the sanitary napkin 2. For the embodiment of the present invention shown in FIGS. 1 to 3 elongation should be between about 110% to about 160%, preferably, between about 115% and about 145%, and, more preferably, about 125% of the length of an unelongated cuff 20.

In the sanitary napkin 2 of the present invention, the cuffs 20a and 20b are formed from a web formed at least partially in a non-planar configuration to provide a "Structural Elastic-Like Film" (SELF) web. A particularly preferred embodiment of a SELF web is a web comprising a thermoplastic film, especially, a polyolefinic film such as a polyethylene film, which includes, in a suitable combination, formed portions formed in a non-planar configuration as described below, and unformed portions retained in a substantially planar configuration. SELF webs are described in detail in copending, commonly assigned U.S. patent application Ser. No. 08/203,087, filed on Feb. 28, 1994 and published as PCT Patent Application Serial No. WO 95/03765, on Feb. 9, 1995. The disclosure of which is incorporated herein by reference. When the cuffs 20a and 20b are produced from a web including formed portions and the longitudinally extending unformed portions as are described below, the contracting action of the cuffs 20a and 20b is generated mainly by the restoring force of the unformed portions, as will be clearly understood from the following description.

As used herein, the term "formed" refers to the creation of a desired structure or geometry upon a web of material that will substantially retain the desired structure or geometry when it is not subjected to any externally applied elongation or forces. Methods suitable for forming a web of material such that the web is transformed into a SELF web include, but are not limited to, embossing by mating plates or rolls, thermoforming, high pressure hydraulic forming, and casting.

Figure 4:
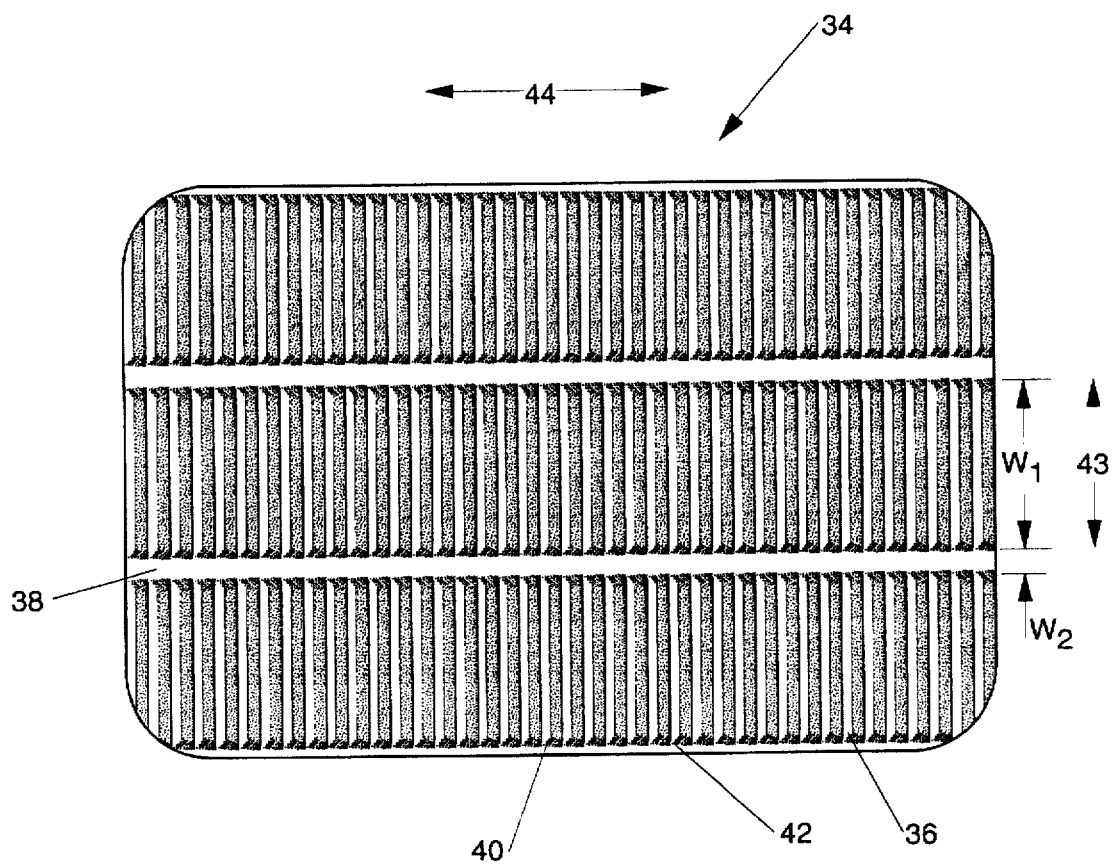
FIG. 4 is a plan view showing a portion of the structural elastic-like film (SELF) web used to form the cuffs of the sanitary napkin illustrated in FIG. 1.
Figure 5:
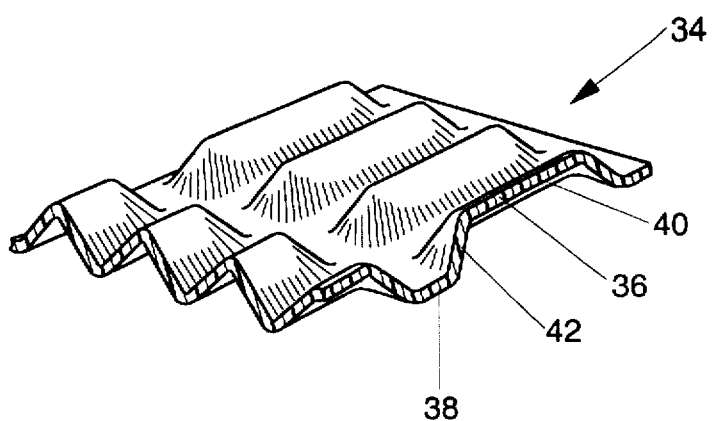
FIG. 5 is an enlarged perspective view showing part of the SELF web illustrated in FIG. 4.

FIGS. 4 and 5 show a web 34 in the form of a SELF web that is suitable for cuffs 20a and 20b. This web 34 comprises formed portions 36 formed in a non-planar configuration as described below, and unformed portions 38 retained in a substantially planar configuration. As is seen clearly in FIG. 4, the formed portions 36 and the unformed portions 38 are arranged alternately in a side-by-side relationship in the transverse direction (shown by double headed arrow 43 in FIG. 4), and extend uninterruptedly in the longitudinal direction (shown by double headed arrow 44 in FIG. 4). As will be understood by reference to FIGS. 4 and 5, the formed portion 36 includes a primary formed portion 40, and secondary formed portions 42 located on both sides in the transverse direction. As seen most clearly in FIG. 5, the primary formed portion 40 takes a substantially uniform, nearly sinusoidal form in its longitudinal cross section, and takes a substantially horizontally extending linear form in its transverse cross section. The secondary formed portion 42 is a region of transition from the primary formed portion 40 and the unformed portion 38.

The proportion of the unformed portions 38 in the web 34 is between about 1% and about 30%, preferably between about 3% and about 20%, more preferably between about 5% and about 12%, when calculated as the ratio of the respective areas (assuming that the web 34 is in a non-elongated state and the area occupied by formed portions 36, including the primary formed portions 40 and the secondary formed portions 42, is projected to the plane of unformed portion 38). This is illustrated by the projection shown in the non-elongated plan view of FIG. 4. In other words, the proportion of the formed portions 36 (including the primary formed portions 40 and the secondary formed portions 42) in the web 34 is between about 70% and about 99%, preferably between about 80% and about 97%, and more preferably between about 88% and about 95%. If the proportion of the unformed portions 38 in the web 34 is too high, the force required to elongate the cuffs 20a and 20b tends to become too high. If the proportion of the unformed portions 38 in the web 36 is too low, the contractive force of the cuffs 20a and 20b is minimal, making it difficult to shape the sanitary napkin 2 into the desired cup-like configuration.

Furthermore, since the formed portions 36 are in a non-planar configuration, they touch the skin of the sanitary napkin 2 wearer only locally at a plurality of small spaced apart regions. Consequently, the discomfort they may cause to the wearer is limited because the sanitary napkin 2 can "breathe". In contrast, if the proportion of the unformed portions 38 is too high and the unformed portions 38 are the main source of contact between the sanitary napkin 2 and the wearer's skin, the unformed portions 38 in a planar configuration touch the wearer's skin uninterruptedly over a relatively large area. Thus, they may cause discomfort to the wearer. Generally, as can be seen in FIG. 4, the width $W_1$ of the formed portion 36 is 0.25 to 50.80 mm (0.01 to 2.00 inches), preferably, 3.18 to 25.40 mm (0.13 to 1.00 inch), while the width $W_2$ of the unformed portion 38 is 0.25 to 12.70 mm (0.01 to 0.50 inch), preferably, 0.76 to 6.35 mm (0.03 to 0.25 inch).

Figure 6:
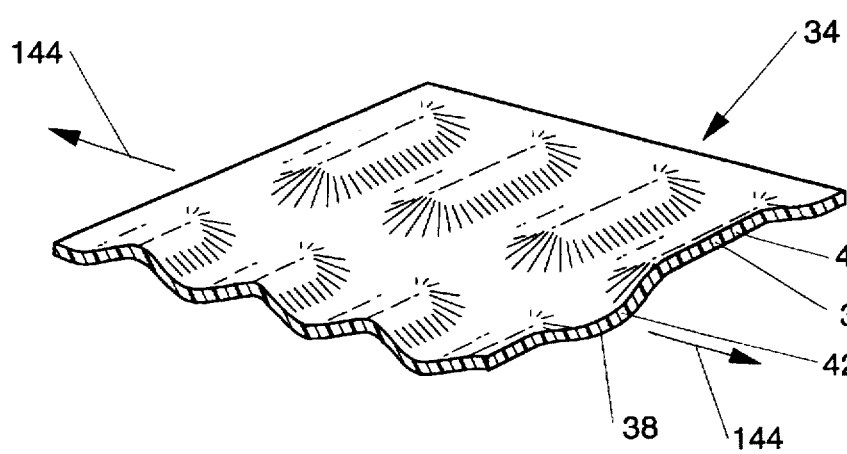
FIG. 6 is an enlarged perspective view showing part of the SELF web illustrated in FIG. 4 in an elastically somewhat elongated state.
Figure 7:
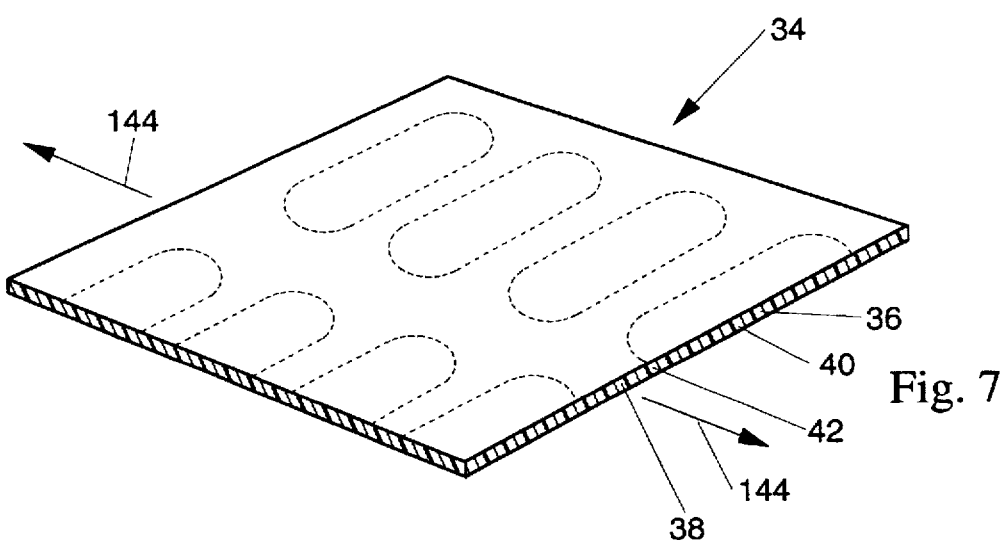
FIG. 7 is an enlarged perspective view showing part of the SELF web illustrated in FIG. 4 in a more elastically elongated state than the state of FIG. 6.

The web 34 shown in FIGS. 4 and 5 exhibits desirable "elastic-like" behavior when the cuffs 20a and 20b are stretched in the longitudinal direction indicated by double headed arrow 44. When a longitudinal stretching force 144 is exerted on the web 34, its cross sectional configuration is geometrically changed as illustrated in FIG. 6, with the amplitude of the formed portions 36 being gradually decreased. Upon a further elongation, the web 34 becomes substantially planar as shown in FIG. 7. During the change of the formed portions 36 from the state illustrated in FIG. 5, to the state in FIG. 6, and, finally, to the state shown in FIG. 7, the force contribution of the formed portions 36 to the total force resisting the elongation is markedly low. The unformed portions 38, on the other hand, are elongated by molecular-level deformation of the constituent material itself, and the resistive force of the web 34 to elongation is mainly provided by the unformed portions 38. In other words, in the range where the elongation of the formed portions 36 is attributable to geometric deformation, rather than to the molecular-level deformation of the material itself, the contracting action of the web 34 upon release of a stretching force exerted on the web 34 results mainly from the contracting action due to molecular-level deformation of the unformed portions 38.

Figure 8:
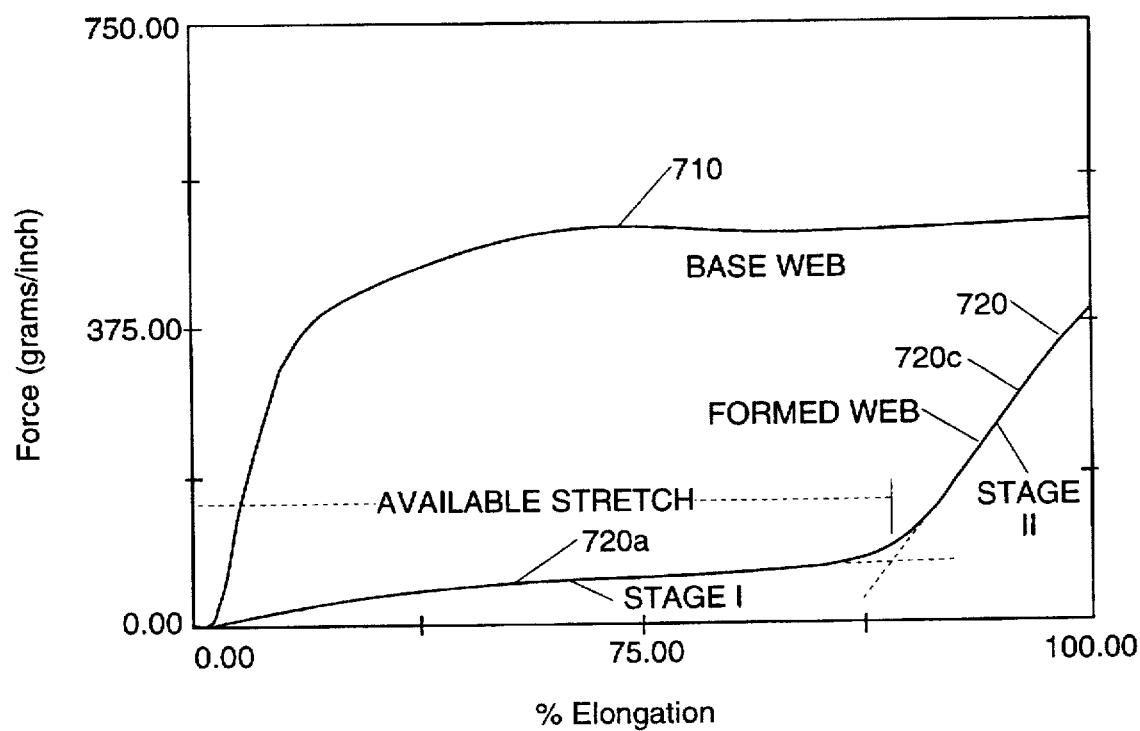
FIG. 8 is a diagram showing the relationship between a longitudinally exerted tensile force and elongation in the formed SELF web illustrated in FIG. 4, and the relationship between a longitudinally exerted tensile force and elongation in an ordinary flat base web before being formed into the SELF web of FIG. 4.

An alternative way of describing this behavior is shown in FIG. 8, which shows the relationship between a longitudinally exerted tensile force and elongation for a SELF web 34, such as is shown in FIGS. 4 and 5. Curve 710 depicts the results of measurements of a longitudinally exerted tensile force and the resulting elongation for a web comprising only unformed portions (i.e., an unconverted or base web). Specifically, the web elongated to generate Curve 710 comprised a linear low density polyethylene film, approximately 1 mil (0.025 mm) in thickness, designated SOFFLEX 1401 which is available from Clopay Corp., Cincinnati, Ohio. Curve 720 shows similar measurements for a formed or SELF web comprising the same linear low density polyethylene film as was used for the film of curve 710. As can be seen in curve 720, the SELF web 34 has a two stage tensile profile: Stage I (curve portion 720a) wherein a relatively low tensile force provides a relatively high elongation, and Stage II (curve portion 720c) where a sharply increased tensile force is required to provide a given elongation. In the Stage I elongation range, release of the tensile force results in substantially complete contraction of the web 34 defining the portion of the tensile/elongation curve available to provide elastic-like stretch to the cuffs 20a and 20b. When the web 34 is to be used as a material for cuffs 20a and 20b in the sanitary napkin 2 illustrated in FIGS. 1 to 3, it is important that the elongation of the web 34 be maintained in the Stage I region. Suitable adjustments can be made by varying the shape of curve 720 in FIG. 8. For example, the stress/strain properties of a material to be formed into a SELF web, the relative proportions of the formed portions 36 and the unformed portions 38 in the web 34, and so on all can be varied to vary the shape of curve 720.

Figure 9:
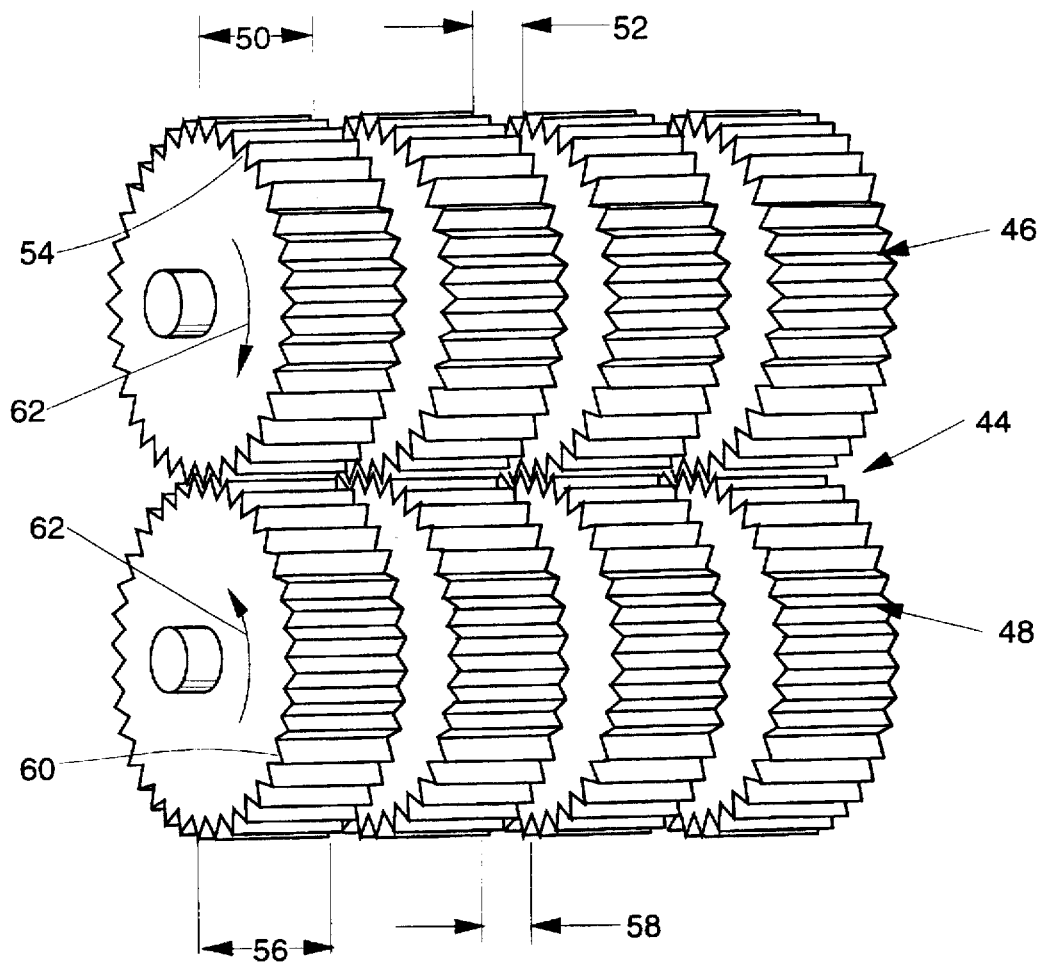
FIG. 9 is a perspective view showing one means suitable for forming the SELF web of FIG. 4.

FIG. 9 shows one processing means 44 that is suitable to convert a planar film web into a SELF web. The processing means 44 includes a pair of rolls sets 46 and 48 which act cooperatively to convert a planar film web into a SELF web. Roll set 46 has toothed regions 50 and grooved regions 52 arranged alternately in the transverse direction, each toothed region 50 having a multiplicity of teeth 54 around its circumference. Similarly, roll set 48 has toothed regions 56 and grooved regions 58 arranged alternately in the transverse direction, each toothed region 56 having a multiplicity of teeth 60 around its circumference. Toothed regions 50 of roll set 46 and the toothed regions 56 of roll set 48 are positioned in mating transverse locations as are the corresponding grooved regions 52 and 58. The mating toothed regions and grooved regions work cooperatively to convert a planar web into a SELF web as follows. When an substantially planar web is fed between roll sets 46 and 48 which are continuously rotating in the direction shown by arrows 62, the portions of the web passing through the toothed regions 50 and 56 are stretched past their yield value by the mating teeth 54 and 60, producing the formed portions 36. The portions of the web passing through the grooved regions 52 and 58 of roll sets 46 and 48 are not stretched, but left in a substantially planar configuration, defining the unformed portions 38. As is obvious to one skilled in the art, the number of and relative degree of engagement of the teeth 54 and 60 and the relative transverse widths of the toothed regions 50, 56 and the grooved regions 52, 58 can be varied to vary the properties of the SELF web 34.

Web materials suitable for conversion into a SELF web 34 are preferably thermoplastic films, particularly polyolefin films, including linear low density polyethylene, low density polyethylene, ultra low density polyethylene, high density polyethylene, polypropylene, or blends of these. Additional suitable web materials include polyester, polyurethanes, compostable or biodegradable polymers, heat shrink polymers, thermoplastic elastomers, metallocene catalyst-based polymers (e.g., INSITE available from Dow Chemical Company Midland, Mich., and Exxact available from Exxon Chemical Corp. Bay City, Tex.), and breathable polymeric films. Also suitable are webs comprising synthetic woven materials, synthetic knit materials, nonwoven materials, apertured films, macroscopically expanded three-dimensional formed films, absorbent or fibrous materials, foams, filled compositions, and laminates and/or combinations thereof.

Figure 10:
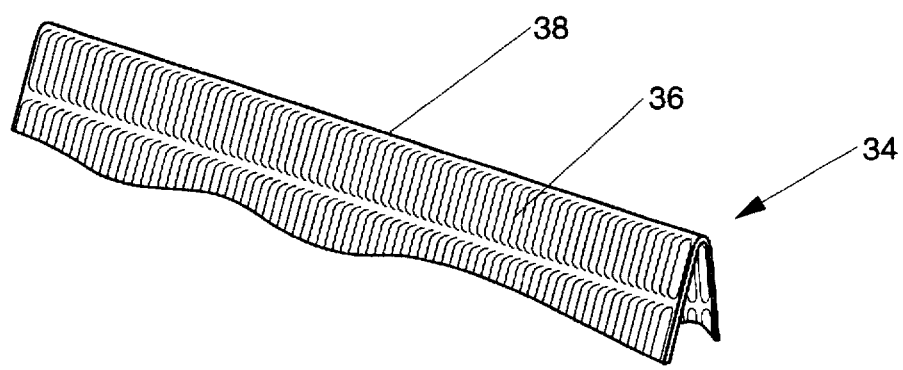
FIG. 10 is a perspective view showing the SELF web of FIG. 4 folded back along the unformed portion.
Figure 11:
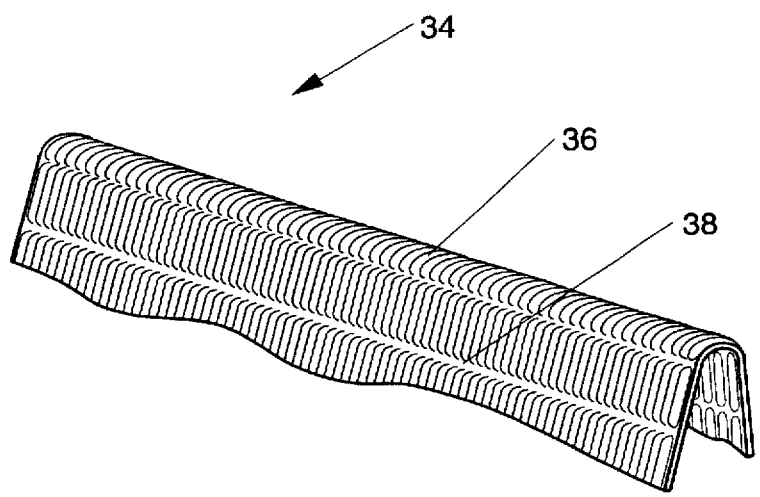
FIG. 11 is a perspective view showing the SELF web of FIG. 4 folded back along the formed portion.

As has been noted above, the cuffs 20a and 20b are folded along longitudinally oriented lines 22a and 22b to provide a two-layer configuration and to form distal edges 23a and 23b. If the cuffs 20a and 20b are formed from the SELF web 34 described in FIGS. 4 to 9, the lines 22a and 22b can extend either along unformed portion 38 as shown in FIG. 10, or along formed portion 36 as shown in FIG. 11. When lines 22a and 22b are extended along the unformed portion 38, the distal edges 23a and 23b become relatively sharp, providing a good seal with the wearer's skin. When lines 22a and 22b are along formed portion 36, the distal edges 23a and 23b are provided with minute "vents" with resulting improved comfort during wear. Preferably the fold lines 22a and 22b are positioned in unformed portion 38 to minimize the risk of lateral leakage of bodily fluids.

As has also been mentioned above, cuffs 20a and 20b are thermally bonded to the topsheet 4 at a plurality of sites for tertiary bonds 28a and 28b in addition to the first bonding means 26a and 26b and second bonding means 27a and 27b which join the cuffs 20a and 20b to the topsheet in the area of peripheral bonding 16. Since the contractive force of the cuffs 20a and 20b is generated mainly by the unformed portions 38 as described above, it is important that the tertiary bonds 28a and 28b be positioned such that the bond area includes unformed portions 38. Also, the bond area for tertiary bonds 28a and 28b should preferably be minimized to minimize the creation of occluding areas that can cause wearer discomfort. One way to minimize the bond area is to provide tertiary bonds 28a and 28b at a plurality sites, each having a relatively small area, which are disposed at spaced apart locations instead of providing one bond 28a and one bond 28b each having a relatively large area at each end of each of the cuffs 20. Such a multi-site configuration for tertiary bonds 28a and 28b is shown in FIGS. 1 and 2.

Figure 12:
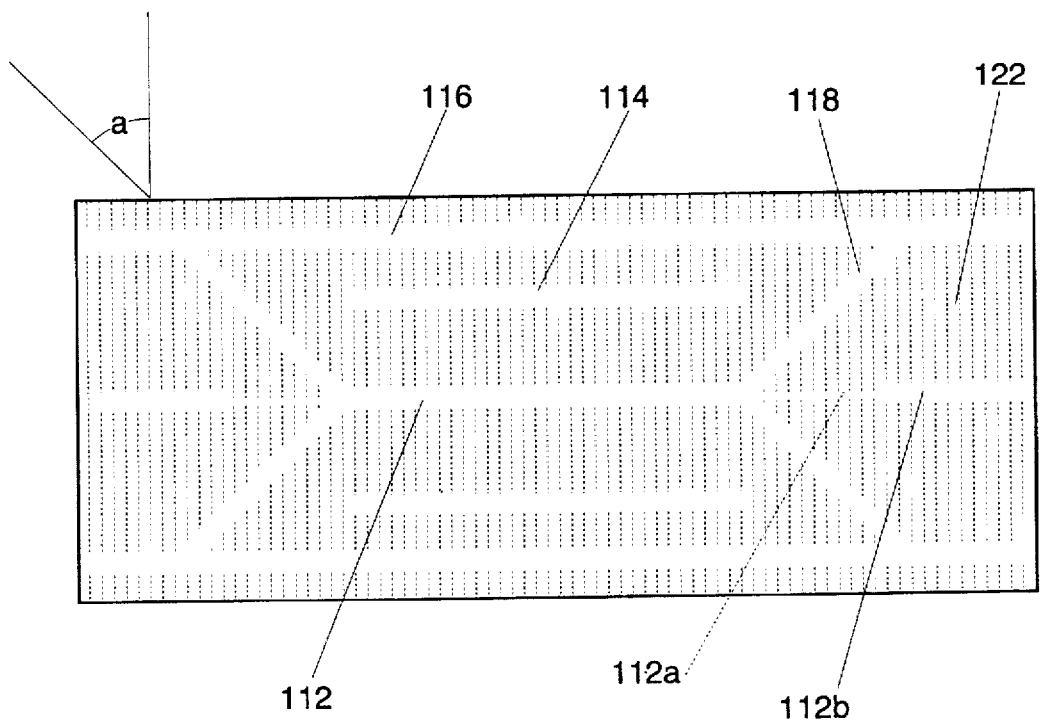
FIG. 12 is a plan view, similar to FIG. 4, showing a preferred embodiment of a SELF web.
Figure 13:
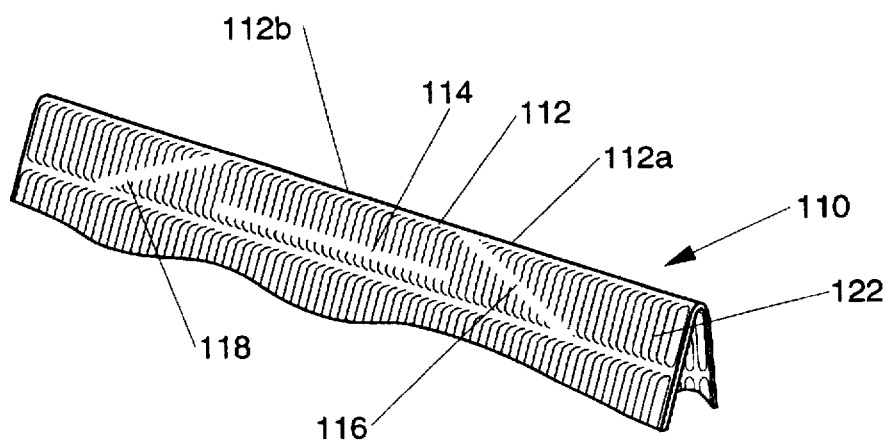
FIG. 13 is a perspective view of the SELF web illustrated in FIG. 12 which has been folded back along the unformed portion.

A particularly preferred pattern relationship between the formed portions and the unformed portions of a SELF web is shown in plan view in FIG. 12 and in perspective view in FIG. 13. FIG. 12 shows a SELF web 110 that not only comprises laterally oriented formed portions 122 and longitudinally oriented unformed portions (fold line 112, hinge 114, and longitudinal band 116) but also diagonally oriented angled band 118. As is shown most clearly in FIG. 12, angled band 118 is disposed at an angle a with respect to a line parallel to the formed portions 122. As can also be seen in FIG. 12, the web is symmetrical about the fold line 112.

Figure 14:
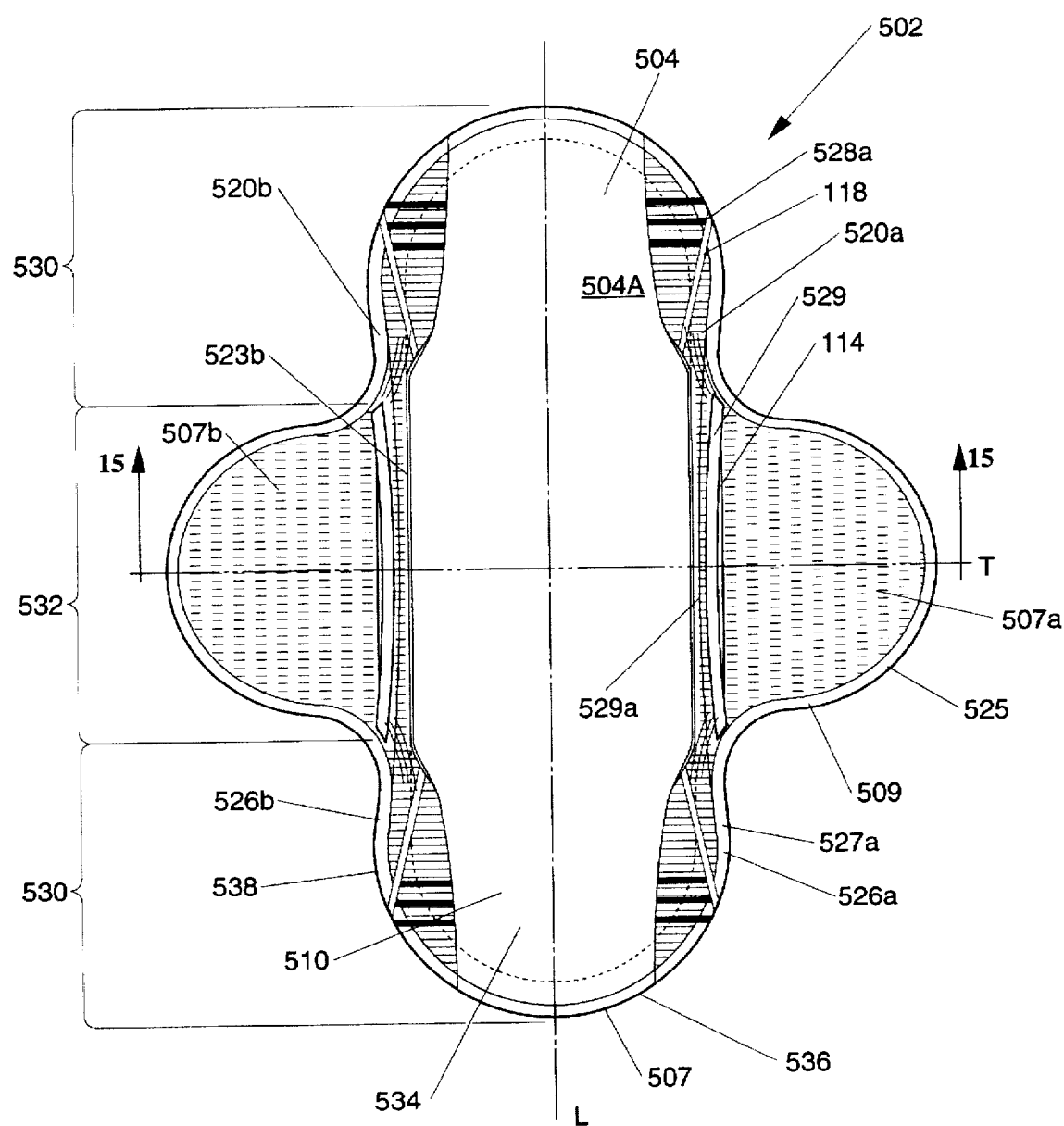
FIG. 14 is a plan view of an alternative embodiment of a sanitary napkin in its flat-out state with the cuffs elongated and which incorporates the SELF web illustrated in FIG. 12.

As can be seen in FIG. 14, such a web is suitable for use as a cuff 520 of sanitary napkin 502. When web 110 is folded about fold line 112 as is described above and shown in FIG. 13, the distal edge 523 of cuff 520 is formed. The cuff 520 is then extended, disposed on, and joined to the body surface 504A of composite topsheet 504 as described above.

Angled band 118 provides a cuff, such as cuff 520 shown in FIG. 14, with a hi-directional force vector that causes cuff 520 to rotate about hinge 114 in a direction outward from centerline L with a resulting lifting of the distal edge 523 of cuff 520 in the vertical or "z" direction with respect to the body surface 504A of composite topsheet 504 even when the sanitary napkin 520 is in a substantially flat-out configuration. The angle a (shown in FIG. 12) is particularly important with respect to the degree of lifting provided by angled band 118. For example, if angle a is about 30 degrees (i.e. about 60 degrees with respect to the longitudinal centerline L), there is insufficient lifting force to cause the distal edge 523 to be displaced upward when the sanitary napkin 502 is in a substantially flat-out configuration. (Such a substantially flat-out configuration is encountered during sanitary napkin use by medium to large size wearers.) Preferably, the angle a is between about 45 degrees and about 75 degrees (i.e. between about 15 degrees and about 45 degrees with respect to the longitudinal centerline L). in a particularly preferred embodiment, the angle a is about 60 degrees (i.e. about 30 degrees with respect to the longitudinal centerline L).

The spacing between the fold line 112 and the hinge 114 is also important. Formed portions 122 create laterally oriented pleats which resist bending. If the spacing between fold line 112 and hinge 114 is too small there is insufficient bending resistance against externally applied forces such as those encountered during the wear cycle and the cuff 520 would tend to fold over and inward during use. Said another way, longitudinally directed unformed portions provide a preferential fold line and, if such unformed fold lines are positioned between the arcuate seal 529 and the distal edge 523 of the cuff 520, unacceptable fold over may occur. It has been found that a spacing between fold line 112 and hinge 114 of between about 0.3 inches (8 millimeters) and about 0.6 inches (16 millimeters) is satisfactory. Particularly preferred is a spacing of about 0.5 inches (12 millimeters) between the fold line 112 and the hinge 114. It is also important that, whatever spacing is used, the spacing is greater than the cuff height. This is shown most clearly in FIG. 14 wherein hinge 114 is positioned outboard of the arcuate seal 529.

Figure 16:
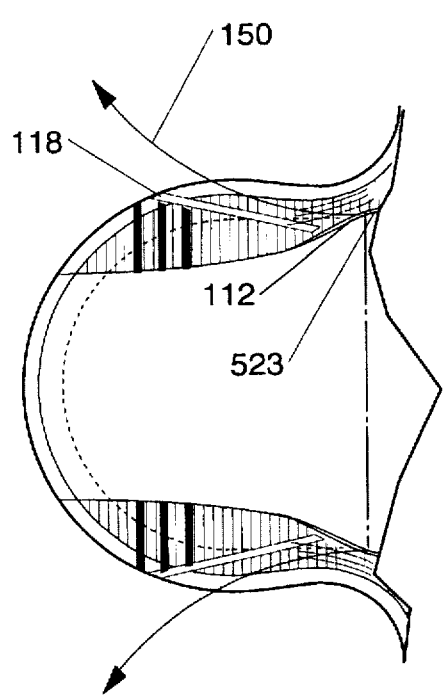
FIG. 16 is a diagrammatic representation of how a line of contractive force is carried through the cuff of the sanitary napkin illustrated in FIG. 14.

It is also important that angled band 118 intercept both the fold line 112 and the longitudinal band 116. This intersection of bands causes the line of tension that causes the distal edge 523 of cuffs 520 to be elevated above the body surface, 504A of composite topsheet 504 to be carried through the fold line 112 to the angled band 118 for transfer to underlying layers of the sanitary napkin 502 in end regions 530. This is shown most clearly in FIG. 16 which shows how the line of tension 150 is directed along the various unformed portions of the preferred SELF web.

As can also be seen in FIG. 12, fold line 112 comprises two portions 112a and 112b. While both portions are unformed, portion 112a is substantially narrower than portion 112b. The narrower unformed portion 112a helps insure that the line of tension is carried along angled band 118 rather than continuing along the distal edge 523 (i.e. fold line 112) since portion 112a will stretch more readily in response to an applied force. However, it is necessary that fold line 112 be continuous to enable web 110 to be folded to form cuff 520 and distal-edge 523 in a reliable manner.

Figure 15:
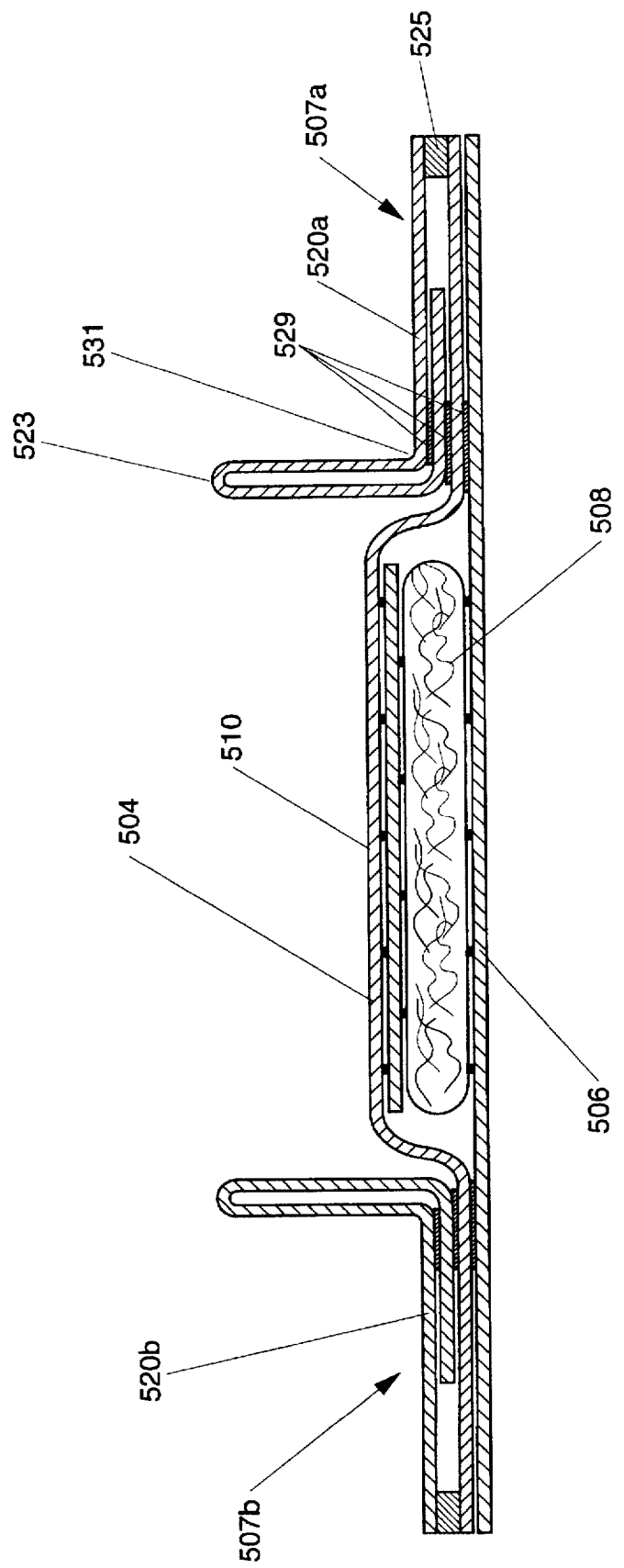
FIG. 15 is a cross sectional view, similar to FIG. 3, of the sanitary napkin illustrated in FIG. 14 taken along line 15—15.

This preferred embodiment of a SELF web is further illustrated in FIGS. 14 and 15 which show, in addition to cuffs comprising an angled band 118, an alternative embodiment of the present invention, sanitary napkin 502 as having two flaps 507a and 507b each of which are adjacent to and extend laterally from the side edge of the absorbent core in at least a central region 532. The flaps are configured to drape over the edges of the wearer's panties in the crotch region so that the flaps are disposed between the edges of the wearer's panties and the thighs. The flaps serve at least two purposes. First, the flaps help serve to prevent soiling of the wearer's body and panties by menstrual fluid, preferably by forming a double wall barrier along the edges of the panty. Second, the flaps are preferably provided with attachment means on their garment surface so that the flaps can be folded back under the panty and attached to the garment facing side of the panty. In this way, the flaps serve to keep the sanitary napkin properly positioned in the panty. The flaps can be constructed of various materials including materials similar to the topsheet, backsheet, tissue, or combination of these materials. Further, the flaps may be a separate element attached to the main body of the napkin or can comprise extensions of one or more of the topsheet, the backsheet, and the cuffs (i.e., unitary). A number of sanitary napkins having flaps suitable or adaptable for use with the sanitary napkins of the present invention are disclosed in U.S. Pat. No. 4,687,478 entitled "Shaped Sanitary Napkin With Flaps", which issued to Van Tilburg on Aug. 18, 1987; U.S. Pat. No. 4,589,876 entitled "Sanitary Napkin", which issued to Van Tilburg on May 20, 1986; and U.S. Pat. No. 4,608,047, entitled "Sanitary Napkin Attachment Means", which issued to Mattingly on Aug. 26, 1986. The disclosure of each of these patents are incorporated herein by reference.

FIGS. 14 and 15 show this alternative embodiment of the present invention, sanitary napkin 502. As can be seen in FIG. 14, the sanitary napkin 502 comprises a main body portion 534 and a pair of laterally extending flaps 507a and 507b. The main body portion 534 is defined by end edges 536 and side edges 538. A portion of each side edge 538 comprises an arcuate seal 529. The sanitary napkin 502 further comprises a central region 532 and two end regions 530.

Flaps 507a and 507b lie in at least the central region 532 of the sanitary napkin 502 and extend laterally outward beyond the side edge 538. As noted above, the flaps may be folded about the leg elastics of a wearer's panties and joined to the outside surface of the panties. Preferably, as also noted above, a pressure sensitive adhesive (not shown) may be disposed on the garment surface of flaps 507a and 507b adjacent the distal edge thereof (i.e., the surface which contacts the outside surface of the wearer's panties when the flaps are folded back) to separably join the flaps to the wearer's panties. The pressure sensitive adhesive may be covered with a silicon-coated paper (not shown) prior to use. Suitable materials are described above with respect to sanitary napkin 2.

As is best shown in FIG. 15, each of the flaps 507a and 507b preferably comprises an extension of the primary topsheet layer 510, the backsheet 508, and a portion of the cuff 520. The components of each flap 507 are joined to each other adjacent the main body portion 534 by arcuate seal 529. Arcuate seal 529 can comprise any sealing means known to the art such as ultrasonic welding, adhesive bonding, or other means known to the art. Thermal bonding is particularly preferred for forming arcuate seal 529. The components of each flap 507 are joined about the periphery 509 of the flap 507 by flap seal 525. While flap seal 525 may comprise any of the means discussed above as suitable for forming the arcuate seal 529, a preferred means is to use a combination of heat and pressure commonly known to the art as crimping to form flap seal 525.

Alternatively, the flaps 507 can comprise separate elements that are joined to one of composite topsheet 504, the backsheet 508, or both composite topsheet 504 and the backsheet 506 using means known to those skilled in the art such as ultrasonic welding, adhesive bonding, or other means known to the art. Each of the flaps 507a and 507b may comprise any suitable material. For example, flaps 507a and 507b may comprise the same material as used for the primary topsheet layer 510 of composite topsheet 504 or the same material as used for backsheet 506. If desired, the flaps 507a and 507b may comprise a SELF material similar to that used for cuffs 520a and 520b. In this case, they may be bonded to the backsheet 506 in a non-elongated state or with slight longitudinal elongation. Preferably for such an embodiment, the flaps 507a and 507b comprise the same material used for the primary topsheet layer 10 as described above.

The cuffs 520 are formed, disposed on, and joined to the main body portion 534 in substantially the same manner as described above with respect to the sanitary napkin 2 of the present invention. That is, the proximal edges 531 of the cuffs 520 are joined along those portions of the side edges 538 that do not comprise the arcuate seal 529 and along portions of the end edges 536 using first bonding means 526 and second bonding means 527. The arcuate seal 529 further joins the proximal edge 531 of the cuff 520 to the main body portion 534. Those portions of each cuff 520 lying in the end regions 530 are further provided with tertiary bonds 528. Preferably, the cuffs 520 are elongated to between about 110% and about 160% of their unstretched length before being disposed on and joined to the central absorbent body 534. More preferably the cuffs 520 are elongated to about 125% of their unstretched length before being disposed on and joined to the main body portion 534. Cuff height can be between about 3 millimeters and about 15 millimeters. Preferably cuff height is between about 6 millimeters and about 12 millimeters. A particularly preferred cuff height is about 8 millimeters. As used herein, the term "cuff height" is intended to mean the distance along the transverse centerline T between the proximal edge and the distal edge of a cuff.

The remaining components of sanitary napkin 502, as illustrated in FIGS. 14 and 15, are substantially the same in construction as those of sanitary napkin 2, as depicted in FIGS. 1 to 3, and are, thus, described in detail above and shown with the same reference number with the corresponding reference number preceded by a 5.

To use a sanitary napkin 502 of the present invention, a wearer would first remove any release liner that has been provided and position the sanitary napkin 502 in the crotch region of her panties, insuring that the flaps 507 are folded over the leg elastics of the panties and that any attachment means provided are used to join the sanitary napkin to the panty. She would then pull the panties on in the normal manner.

The disclosures of all patents, patent applications (and any patents which issue thereon, as well as any corresponding published foreign patent applications), and publications mentioned throughout this patent application are hereby incorporated by reference herein. It is expressly not admired, however, that any of the documents incorporated by reference herein teach or disclose the present invention. It is also expressly not admitted that any of the commercially available materials or products described herein teach or disclose the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a longitudinal centerline extending in a longitudinal direction, a pair of opposing side edges, a pair of ends, and a longitudinally extending central portion, said central portion defining a plane, said absorbent article further comprising:

a liquid pervious topsheet;

a liquid impervious backsheet joined to said topsheet;

an absorbent core positioned between the topsheet and the backsheet; and a pair of bands of web material, each having a distal edge, said bands being comprised of a first region and a second region, one of said bands of web material being arranged adjacent each of said side edges of the absorbent article and joined to at least one of the topsheet and the backsheet in a longitudinally elastically elongated state, said first and second regions of said bands of web material being visibly distinct from each other wherein said second region comprises a plurality of rib elements and said first region comprises at least two substantially planar regions, wherein at least one of said at least two substantially planar first regions is oriented generally in the longitudinal direction, at least one other of said at least two substantially planar first regions is oriented at an angle between about 15 degrees and about 45 degrees to said longitudinal direction, and said plurality of rib elements define ridges that are oriented generally in a transverse direction, said substantially planar first regions providing a contractive force wherein said contractive force causes said ends to extend upwardly inclinedly away from said plane of said central portion, and a bi-directional force vector which causes said distal edges to extend upwardly away from said topsheet along both of said side edges at least in said central portion.

2. An absorbent article according to claim 1 further comprising at least one laterally extending flap joined to one of said side edges in at least said central portion.

3. An absorbent article according to claim 2 wherein said at least one laterally extending flap comprises a pair of flaps, one flap being joined to and extending from each of said side edges in at least said central portion.

4. An absorbent article according to claim 3 wherein said flaps comprise an extension of said topsheet and said backsheet.

5. An absorbent article according to claim 1 wherein said angle is about 45 degrees.

* * * * *

UNITED STATES PATENT AND TRADEMARK OFFICE
CERTIFICATE OF CORRECTION

PATENT NO. : 5,730,738
DATED : March 24, 1998
INVENTOR(S) : Ronald Ray McFall et al.

It is certified that error appears in the above-identified patent and that said Letters Patent is hereby corrected as shown below:

Column 2, line 14, "carded" should read -- carried --.

Column 4, line 25, "region,." should read -- region, --.

Column 4, line 28, "wig" should read -- within --.

Column 4, line 64, "potion" should read -- portion --.

Column 6, line 7, "fills" should read -- films --.

Column 7, line 51, "dearly" should read -- clearly --.

Column 10, line 11, "are same the" should read -- are the same --.

Column 17, line 41, "admired," should read -- admitted, --.

Signed and Sealed this

Twenty-fifth Day of April, 2000

Attest:

Q. TODD DICKINSON

*Attesting Officer*　　　　　*Director of Patents and Trademarks*